US008349567B2

(12) United States Patent
Gebauer et al.

(10) Patent No.: US 8,349,567 B2
(45) Date of Patent: Jan. 8, 2013

(54) CATHEPSIN C-BASED SCREENING METHODS FOR IDENTIFYING MODULATORS OF PAIN

(75) Inventors: Mathias Gebauer, Frankfurt am Main (DE); Martin Michaelis, Frankfurt am Main (DE); Danping Ding-Pfennigdorff, Frankfurt am Main (DE); Anke Schulte, Frankfurt am Main (DE); Christiane Metz-Weidmann, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 12/934,178

(22) PCT Filed: Mar. 21, 2009

(86) PCT No.: PCT/EP2009/002091
§ 371 (c)(1),
(2), (4) Date: Dec. 10, 2010

(87) PCT Pub. No.: WO2009/118137
PCT Pub. Date: Oct. 1, 2009

(65) Prior Publication Data
US 2011/0091888 A1 Apr. 21, 2011

(30) Foreign Application Priority Data
Mar. 26, 2008 (EP) ..................... 08290285

(51) Int. Cl.
*C12Q 1/68* (2006.01)
*C12Q 1/66* (2006.01)
(52) U.S. Cl. ............ 435/6.13; 435/6.1; 435/6.18; 435/8
(58) Field of Classification Search ........................ None
See application file for complete search history.

(56) References Cited

U.S. PATENT DOCUMENTS

| 4,816,397 | A | 3/1989 | Boss et al. |
| 4,816,567 | A | 3/1989 | Cabilly et al. |

FOREIGN PATENT DOCUMENTS

| EP | 0 368 684 | | 5/1990 |
| EP | 0889723 | | 3/1997 |
| EP | 0852493 | | 4/1997 |
| EP | 0916336 | A1 | 5/1999 |
| EP | 0944398 | B1 | 4/2004 |
| WO | WO 88/01649 | | 3/1988 |
| WO | WO 93/06213 | | 4/1993 |
| WO | WO 98/24884 | | 6/1998 |
| WO | WO 03/020287 | A2 | 3/2003 |
| WO | WO 2004/077053 | A1 | 9/2004 |
| WO | WO 2005/113789 | A2 | 5/2005 |
| WO | WO 2005/106012 | A2 | 11/2005 |
| WO | WO 2006/122237 | A2 | 11/2006 |
| WO | WO 2007/045476 | A2 | 4/2007 |

OTHER PUBLICATIONS

Wells, J.A. (1990). Additivity of mutational effects in proteins. Biochemistry. 29(37):8509-8517.*

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
International Search Report WO2009/118137A1 dated Oct. 1, 2009.
Adkison et al., Dipeptidyl peptidase I activates neutrophil-derived serine proteases and regulates the development of acute experimental arthritis. J. of Clinical Investigations. 2002. vol. 109, pp. 363-371.
Baugh et al., Quantitative analysis of mRNA amplification by in vitro transcription, Nucleic Acids Research, vol. 29, No. 5, pp. 5, e29, pp. 1-9, 2001.
Cigic et al., The Residual Pro-Part of Cathepsin C Fulfills the Criteria Required for an Intramolecular Chaperone in Folding and Stabilizing the Human Proenzyme, Biochemistry, vol. 39, 2000, pp. 12383-12390.
De Haar et al., Loss-of-funtion Mutations in Cathepsin C in Two Families With Papillon-Lefevre Syndrome are Associated With Deficiency of Serine Proteinases in PMNs, Human Mutation, Mutationin Brief (Online, 2004.
Deleo et al., Transgenic expression of TNF by astrocytes increases mechanical allodynia in a mouse neuropathy model, Neuroreport, vol. 11, No. 3, Feb. 28, 2000, pp. 599-602.
Diamond et al, Monoclonal Antibodies, New England Journal of Medicine, vol. 304, No. 22, May 28, 1981, pp. 1344-1349.
Henningsson et l., Mast Cell cathepsins C and S control levels of carboxypeptidase A and the chymase, mouse mast cell protease 5, Biological Chemistry, 2003, vol. 384, pp. 1527-1531.
Heusel et al., Cytotoxic Lymphocytes Require Granzyme B for the Rapid Induction of DNA Fragmentation and Apoptosis in Allogeneic Target Cells, Cell, vol. 76, Mar. 25, 1994, pp. 977-987.
Julius et al., Molecular mechanisms of nociception, Nature, vol. 413, 2001, pp. 203-309.
Mansour et el., Disruption of the proto-oncogene int-2 in mouse embryo-derived stem cells: a general strategy for targeting mutations to non-selectable genes, Nature, vol. 336, Nov. 24, 1998, pp. 348-352.
McGuire et al., Generation of Active Myeloid and Lymphoid Granule Serino Proteases Requires Processing by the Granule Thiol Protease Dipeptidyl Peptidase I. J. of Biol. Chem, vol. 268, Feb. 5, 1993, pp. 2458-2467.
Paris et al., Molecular cloning and sequence analysis of human preprocathepsin C. FEBS Letters, 1995, vol. 369, pp. 326-330.
Pham et al., Dipeptidyl peptidase I is required for the processing and activation of granzymes A and B in vivo, PNAS, vol. 96, Jul. 1998, pp. 8627-8632.
Pham et al., Molecular Cloning, Chromosomal Localization, and Expression of Murine Dipeptidyl Peptidase I, J of Biol. Chem., vol. 272. No. 16, Apr. 18, 1997, pp. 10696-10703.
Pham et al., Papillon-Lefe'vre Syndrome: Correlating the Molecular, Cellular, and Clinical Consequences of Cathepsin C/Dipeptidyl Peptidase I Deficiency in Humans1, J. of Immunology. vol. 173, 2004, pp. 7277-7281.

(Continued)

*Primary Examiner* — Christine J Saoud
*Assistant Examiner* — Jon M Lockard
(74) *Attorney, Agent, or Firm* — Nicole L. M. Parsons

(57) ABSTRACT

Present invention concerns the use of Cathepsin C. Other aspects of the invention concern methods for screening pharmaceuticals, for diagnosing pain susceptibility and for the treatment of pain.

7 Claims, 7 Drawing Sheets

OTHER PUBLICATIONS

Figure 1:
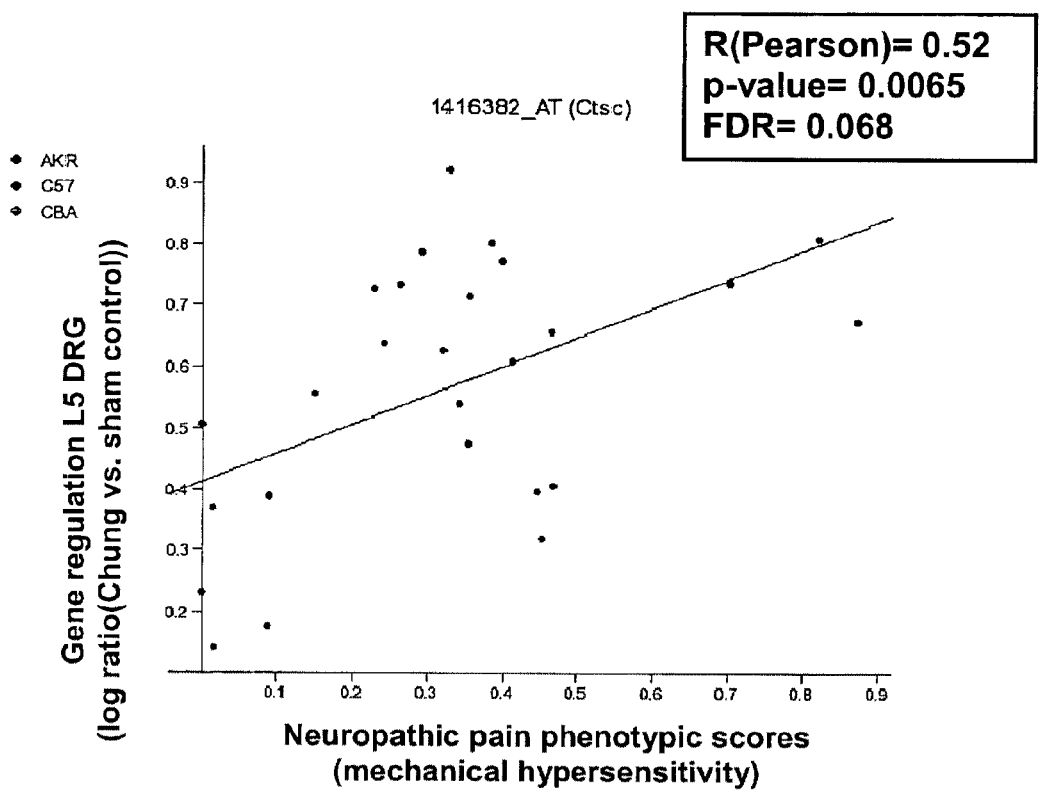

Rao et al., Human Dipeptidyl-peptidase I, J. of Biol. Chem. vol. 272, Apr. 11, 1997, pp. 10260-10265.

Scholz, Joachim, et al., Can we conquer pain?, Nature Neuroscience. (2002), vol. 5, pp. 1062-1067.

Sheth et al., Inhibition of dipeptidyl peptidase I in the human mast cell line HMC-1: blocked activation of tryptase, but not of the predominant chymotryptic activity, Biochemical Pharmacology, vol. 66, 2003, pp. 2251-2262.

Soriano et al., Targeted Disruption of the c-src Proto-Oncogene Leads to Osetopetrosis in Mice, Cell, vol. 54, Feb. 22, 1991, pp. 693-702.

Storey, J., A direct approach to false discovery rates, J.R. Statist. Soc. B. vol. 64, Part 3. 2002, pp. 479-498.

Szabo et al., Role of Transient Receptor Potential Vanilloid 1 Receptors in Adjuvant-Induced Chronic Arthritis: In Vivo Study Using Gene-Deficient Mice, J. of Pharmcol and Exp. Therapeutics, vol. 314, No. 1, 2005, pp. 111-119.

Toomes et al., Loss-of-function mutations in the cathepsin C gene result in periodontal disease and palmoplantar keratosis, Nature Genetics, vol. 23, 1999, pp. 421-424.

Turk et al., Lysosomal cysteine proteases: more than scavengers, Biochimica et Biophysica Acta, 2000, vol. 1477, pp. 98-111.

Winter et al., Man-made antibodies, Nature, vol. 349, Jan. 24, 1991, pp. 293-299.

Wolters et al., Dipeptidyl Peptidase I is Essential for Activation of Mast Cell Chymases, but Not Tryptases, In Mice, J. of Biol. Chem., vol. 276, May 25, 2001, pp. 18551-18556.

Wolters et al., Regulated Expression, Processing, and Secretion of Dog Mast Cell Dipeptidyl Peptidase I, J. of Biol. Chem., vol. 273, No. 25, Jun. 19, 1998, pp. 15514-15520.

Wood, John N., Pathobiology of Visceral Pain: Molecular Mechanisms and Therapeutic implications II. Genetic approaches to pain therapy, Am. J. Physiol Gastrointest Liver Physiol, (2000), vol. 278, pp. G507-G512.

Woolf, Clifford J. et al., Neuronal Plasticity: Increasing the Gain in Pain, Science, (2000), vol. 288. pp. 1765-1768.

Woolf, Clifford J. et al., Neuropathic pain: aetiology, symptoms, mechanisms, and management, The Lancet, (1999), vol. 353, pp. 1959-1964.

\* cited by examiner

Figure 2      Cathepsin C: Intensity data, L5 DRG, 3d p.o.
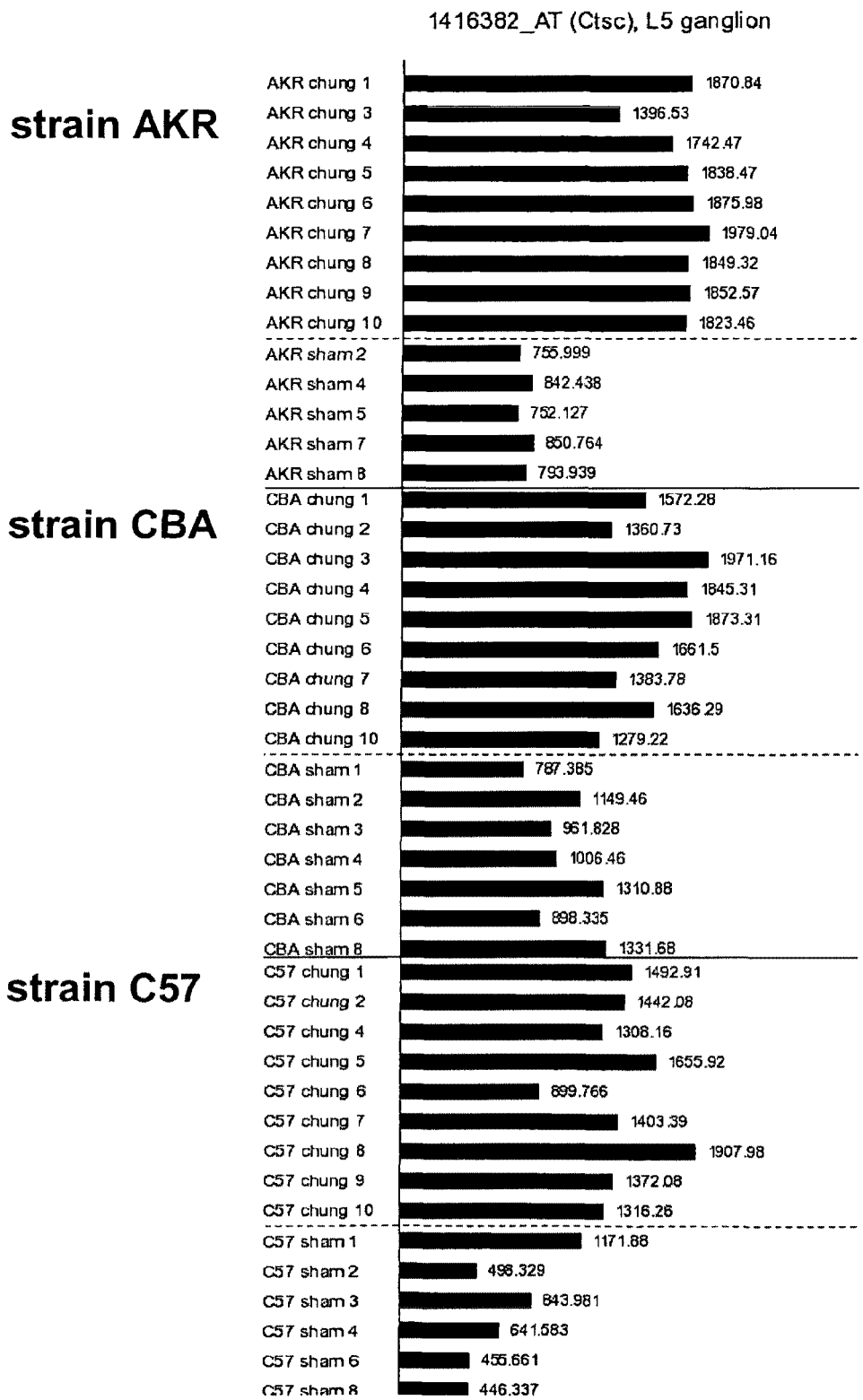

Figure 3: fragment of mouse Cathepsin cDNA

```
gctgttttgcttgtgggctatggaagagatccagttactgggatagaatactggattata
aagaacagctggggctctaactggggggagagtggctacttccgtatccgcagaggaact
gatgaatgtgcaattgagagtatagccgtggcggccnataccgattcctaaattatagga
catagctcccagtgttacatacgggtctttatcactcacagagtgatttagtcacatgct
gaagactttttcagagcaatatcagaagcttaccactaagcatctttaaagaattttgtc
tttgaacttaaaaccatccttgattttttcttttaatatcttccccatcaactactgaa
```

SEQ ID NO: 7

Figure 4: Cathepsin C human mRNA sequence

```
   1 cgtagctatt tcaaggcgcg cgcctcgtgg tggactcacc gctagcccgc agcgctcggc
  61 ttcctggtaa ttcttcacct cttttctcag ctccctgcag catgggtgct gggccctcct
 121 tgctgctcgc cgccctcctg ctgcttctct ccggcgacgg cgccgtgcgc tgcgacacac
 181 ctgccaactg cacctatctt gacctgctgg gcacctgggt cttccaggtg ggctccagcg
 241 gttcccagcg cgatgtcaac tgctcggtta tgggaccaca agaaaaaaaa gtagtggtgt
 301 accttcagaa gctggataca gcatatgatg accttggcaa ttctggccat ttcaccatca
 361 tttacaacca aggctttgag attgtgttga atgactacaa gtggtttgcc tttttttaagt
 421 ataaagaaga gggcagcaag gtgaccactt actgcaacga caatgact gggtgggtgc
 481 atgatgtgtt gggccggaac tgggcttgtt tcaccggaaa gaaggtggga actgcctctg
 541 agaatgtgta tgtcaacata gcacacctta agaattctca ggaaaagtat tctaataggc
 601 tctacaagta tgatcacaac tttgtgaaag ctatcaatgc cattcagaag tcttggactg
 661 caactacata catggaatat gagactctta ccctgggaga tatgattagg agaagtggtg
 721 gccacagtcg aaaaatccca aggcccaaac ctgcaccact gactgctgaa atacagcaaa
 781 agattttgca tttgccaaca tcttgggact ggagaaatgt tcatggtatc aattttgtca
 841 gtcctgttcg aaaccaagca tcctgtggca gctgctactc atttgcttct atgggtatgc
 901 tagaagcgag aatccgtata ctaaccaaca ttctcagac cccaatccta agccctcagg
 961 aggttgtgtc ttgtagccag tatgctcaag gctgtgaagg cggcttccca taccttattg
1021 caggaaagta cgcccaagat tttgggctgg tggaagaagc ttgcttcccc tacacaggca
1081 ctgattctcc atgcaaaatg aaggaagact gctttcgtta ttactcctct gagtaccact
1141 atgtaggagg tttctatgga ggctgcaatg aagccctgat gaagcttgag ttggtccatc
1201 atgggcccat ggcagttgct tttgaagtat atgatgactt cctccactac aaaaagggga
1261 tctaccacca cactggtcta agagaccctt caacccctt tgagctgact aatcatgctg
1321 ttctgcttgt gggctatggc actgactcag cctctgggat ggattactgg attgttaaaa
1381 acagctgggg caccggctgg ggtgagaatg gctacttccg gatccgcaga ggaactgatg
1441 agtgtgcaat tgagagcata gcagtggcag ccacaccaat tcctaaattg tagggtatgc
1501 cttccagtat ttcataatga tctgcatcag ttgtaaaggg gaattggtat attcacagac
1561 tgtagacttt cagcagcaat ctcagaagct acaaataga tttccatgaa gatatttgtc
1621 ttcagaatta aaactgccct taattttaat atacctttca atcggccact ggccattttt
1681 ttctaagtat tcaattaagt gggaattttc tggaagatgg tcagctatga agtaatagag
1741 tttgcttaat catttgtaat tcaaacatgc tatatttttt aaaatcaatg tgaaaacata
1801 gacttatttt taaattgtac caatcacaag aaaataatgg caataattat caaaactttt
1861 aaaatagatg ctcatatttt taaaataaag ttttaaaaat aactgcaaaa aaaaaaaaaa
1921 aaaa
```

SEQ ID NO:1

Figure 5: Cathepsin C human protein sequence according to Swiss-prot P53634

MGAGPSLLLA ALLLLLSGDG AVRCDTPANC TYLDLLGTWV FQVGSSGSQR DVNCSVMGPQ 70      80      90      100      110      120

EKKVVVYLQK LDTAYDDLGN SGHFTIIYNQ GFEIVLNDYK WFAFFKYKEE GSKVTTYCNE 130      140      150      160      170      180

TMTGWVHDVL GRNWACFTGK KVGTASENVY VNTAHLKNSQ EKYSNRLYKY DHNFVKAINA 190      200      210      220      230      240

IQKSWTATTY MEYETLTLGD MIRRSGGHSR KIPRPKPAPL TAEIQQKILH LPTSWDWRNV 250      260      270      280      290      300

HGINFVSPVR NQASCGSCYS FASMGMLEAR IRILTNNSQT PILSPQEVVS CSQYAQGCEG 310      320      330      340      350      360

GFPYLIAGKY AQDFGLVEEA CFPYTGTDSP CKMKEDCFRY YSSEYHYVGG FYGGCNEALM 370      380      390      400      410      420

KLELVHHGPM AVAFEVYDDF LHYKKGIYHH TGLRDPFNPF ELTNHAVLLV GYGTDSASGM 430      440      450      460

DYWIVKNSWG TGWGENGYFR IRRGTDECAI ESIAVAATPI PKL

SEQ ID NO: 2

Figure 6: Primers for detecting human Cathepsin C cDNA forward: 5'-gctccctgcagcatgggtgctgggccctcc-3' (SEQ ID NO.4)

reverse: 5'-gcataccctacaatttaggaattggtgtgg-3' (SEQ ID NO.5)

Figure 7: Probe for detecting mouse Cathepsin C

GGCCAGTGAATTGTAATACGACTCACTATAGGGAGGCGGT      SEQ ID NO.6

CATHEPSIN C-BASED SCREENING METHODS FOR IDENTIFYING MODULATORS OF PAIN

Present invention concerns the use of Cathepsin C. Other aspects of the invention concern methods for screening pharmaceuticals, for diagnosing pain susceptibility and for the treatment of pain.

In the western world, chronic pain is a major unsolved health problem undermining the health and welfare of millions of citizens. Chronic pain severely afflicts the well-being of the individual experiencing it and it is frequently accompanied or followed by vegetative signs, which often result in depression. Chronic pain results in individual suffering and social economic costs of tremendous extent. Existing pharmacological pain therapies are widely unsatisfying both in terms of efficacy and of safety.

In light of the severe drawbacks connected with state of the art pain treatments, there is a great need for novel options for treatment of ongoing pain, and for diagnosis and prognosis concerning the potential development of chronic pain. Especially in light of the vast gap between the fast advancing understanding of the neurobiology of pain and the unmet clinical need to provide effective treatments without the drawbacks of state of the art treatments, efforts need to be directed to the discovery of new targets for novel classes of analgesics.

Thus, it is the object of the present invention to provide a new means for the development and provision of new classes of pain modulating drugs.

This object is solved by the use of Cathepsin C or functional fragments or derivatives thereof for identifying compounds that modulate pain.

The invention is based on the surprising finding of the inventors, demonstrating for the first time that Cathepsin C expression closely correlates with pain susceptibility in mouse models of neuropathic pain.

Pain is, per definition of the international association for the study of pain, an unpleasant sensory and emotional experience associated with actual or potential tissue damage, or described in terms of such damage. Pain is normally the consequence of an activation of the nociceptive nervous system, that is specialized to detect and encode damage or potential damage of tissue. Pain is thus part of a warning system of the body to initiate reactions for minimizing actual or potential damage to the body. Pain can be the primary symptom of a medical condition or can be secondary effect of a diseased state, often without any biological meaning.

Pain may be acute or chronic. Acute pain is a physiological signal indicating a potential or actual injury. It occurs accompanying tissue damage, infection, inflammation or other acute causes, alerting the individual after bodily damage or malfunction. If acute pain is not treated properly, it may lead to chronic pain.

Chronic pain is a diseased state with varying origin, duration, intensity and specific symptoms.

Chronic pain may be of nociceptive origin, inflammatory or neuropathic. Nociceptive pain is judged to be commensurate with ongoing activation of somatic or visceral pain-sensitive nerve fibers. Neuropathic pain is pain resulting from any kind of damage to peripheral or central neuronal tissue; it is believed to be sustained by aberrant somatosensory processes in the peripheral nervous system, the CNS, or both. (For an overview of pain mechanisms, see for example Scholz and Woolf, 2002; Julius and Basbaum, 2001, Woolf and Mannion, 1999; Wood, J. D., 2000; Woolf and Salter, 2000.)

Chronic neuropathic pain is variable from patient to patient. Recent data indicate that individual pain susceptibility plays an important role for the amount of individual suffering, i.e. there is an important heritable predisposition to pain, particularly to the development of neuropathic pain. Present invention is based on extensive studies of the inventors which aimed to identify pain susceptibility genes (i.e. genes that determine the amount of pain felt in the presence of a given, fixed degree of tissue injury) in rodent models of chronic pain. The rodent models and experimental settings used by the inventors allowed for experimental conditions where among the different individuals a) nature and uniformity of the neural lesion can be precisely controlled and b) genetic and environmental variability can be minimized.

Cathepsin C(CTSC; alternative titles: dipeptidyl(amino) peptidase I, DPPI; (EC 3.4.14.1)), is a lysosomal protease.

The gene locus of Cathepsin C is on chromosome 11q14.1-q14.3 (see Rao et al., 1997). The genomic sequence of Cathepsin C is publicly available at the NCBI nucleotide database under: NW_925129 (genomic sequence comprising the sequence of human Cathepsin C, SEQ ID NO:3) or NW_001030863 (genomic DNA sequence comprising mouse Cathepsin C)

The coding polynucleotide sequence of Cathepsin C is publicly available at the NCBI nucleotide database under several accession numbers, such as: NM_001814 (*Homo sapiens* cathepsin C transcript variant 1 mRNA), BC113897 (complete coding sequence (cds) of *Homo sapiens* cathepsin C, transcript variant 2, mRNA), BC109386 (*Homo sapiens* cathepsin C, mRNA, complete cds), NM_009982 (mus musculus cathepsin C mRNA). The skilled person knows how to retrieve further coding sequences of cathepsin C from the NCBI database (cathepsin C of other species; mutants or different isoforms of cathepsin C, if existing). If in the following, it is referred to the cathepsin C coding sequence, this can mean any of the above mRNA or coding sequences; preferably, the sequence according to reference numbers NM_001814 (human) (SEQ ID NO: 1) or NM_009982 (mouse) is meant.

The protein sequence of Cathepsin C is publicly available at the NCBI protein database, e.g. under the following accession numbers: *homo sapiens* (hs): complete cds: CAA6067, AAL48191, AAL48192, AAL38195, AAH54028, AAQ08887, AAI00893, AAI00894, AAI00892, AAI00895, AAI09387, AAI10072, AAI13851; hs isoform CRA_b: EAW59364; hs isoform CRA_a: EAW59363; hs cathepsin C isoform a preproprotein: NP_001805; hs isoform b precursor: AAI13898 or NP_680475. Murine (mus musculus) cathepsin C: AAH67063; preproprotein: NP_034112; isoform CRA-b (mus musculus): EDL06796; isoforms CRA-a (mus musculus): EDL06795. Moreover the protein sequence is publicly available at the UniProtKB database (www.beta.uniprot.orq), under accession numbers: P53634 (HUMAN_CATC, human Cathepsin C, SEQ ID NO:2), or P97821 (CATC_MOUSE, murine Cathepsin C). If in the following, it is referred to the cathepsin C protein or amino acid sequence, this can mean any of the above protein sequences; preferably, the sequence according to reference numbers P53634 (for the human sequence) or P97821 (for the murine sequence).

NCBI is the national centre for biotechnology information (postal address: National Centre for Biotechnology Information, National Library of Medicine, Building 38A, Bethesda, Md. 20894, USA; web-adress: www.ncbi.nhm.nih.qov). More sequences (e.g. sequences carrying SwissProt or EMBL accession numbers) can be retrieved in the UniProtKB database under www.beta.uniprot.org.

The cloning of hs Cathepsin C is published by Paris et al., 1995, the cloning of murine cathepsin C is published by Pham et. al, 1997. The 5"flanking region (promoter/enhancer) is published by Rao et. al, 1997 (see especially page 10263, FIG. 4 and the detailed text on the lower part of said page, which is incorporated herein by reference; e.g. the gene sequence starting from −1127 up to to +1). Cathepsin C is expressed at high levels in lung, kidney and placenta, and to a lesser extent in a variety of other organs, including cells of the immune system (Rao et. al., 1997).

Cathepsin C is a lysosomal protease capable of removing dipeptides from the amino terminus of protein substrates. Cathepsin C is involved in the activation of granule serine proteases, which are expressed in bone marrow-derived effector cells of the immune system; and it is involved for processing and activation of the T-lymphocyte granzymes A (GZMA) and B (GZMB) and granzyme C; further functions are the processing of different lysosomal cathepsins, the activation of different serine proteases (chymotrypsin-like serine proteases) by removal of an inhibitory N-terminal dipeptide residue (such as the above granzymes, Cathepsin C itself, neutrophil elastase, proteinase-3, mast cell chymase and tryptase (Toomes et al., 1999, Pham and Ley 1999, Turk et al, 2000, Henningsson et al, 2003; McGuire et al., 1993; Adkison et al., 2002; Wolters et al, 2001; Pham et al, 2004; DeHaar et al, 2004; Sheth et al, 2003, Methot et al., 2007). Its functions in general comprise: protease activity, peptidase activity, e.g. dipeptidylpeptidase, exopeptidase or endopeptidase activity; activation of serine proteases (e.g. one or more of the following: elastase, cathepsin G and granzymes A and B, neuraminidase and factor XIII).

Cathepsin C is a 200 kD tetrameric protein (Paris et al., 1995), which stands in contrast to other cathepsins (e.g. cathepsin B, H, L and S) being small monomeric enzymes. The cathepsin C protein is processed from a prepro-form to a proteolytically active enzyme. The mature monomeric form of cathepsin C consists of a heavy chain, a light chain and a propeptide remaining associated with the active enzyme (Wolters et al., 1998; Cigic et al., 2000); four of such cathepsin C monomers forming the proteolytically active, 200 kD cathepsin C tetramer.

The generation of cathepsin C knock-out mice (Dppi-knock out mice) is published by Pham and Ley, 1999 (see materials and methods part, from p. 8627 go 8629 and esp. p. 8627, second half of right column to p. 8628, first half of left column for construction of the DPPI targeting vector and generation of DPPI −/− mice; see as well Heusel et al, 1994; Mansour et al., 1988 and Soriano et al., 1991, to which Pham and Ley, 1999, refers for embryonic stem cell generation).

The use according to present invention allows for the identification of novel substances for the prevention and/or treatment of pain, especially neuropathic pain. The use according to present invention comprises the identification of compounds with desired characteristics (i.e. lowering the pain sensation) as well as the identification of compounds with undesired characteristics (i.e. increasing the pain sensation). Moreover, present invention allows for the further characterisation of compounds already identified of being useful for the prevention and/or treatment of any disease or diseased state. In this case, present invention can e.g. be used for excluding identified active compounds having unwanted side-effects (i.e. the increase of pain sensation): Candidate compounds for a given disease can e.g. be profiled for their influence on Cathepsin C (protein and/or nucleic acid, expression and/or function, etc.).

A compound/test compound/active compound as to be employed for the different aspects of present invention can be any biological or chemical substance or natural product extract, either purified, partially purified, synthesized or manufactured by means of biochemical or molecular biological methods.

A compound considered as being active in modulating pain in the sense of the different aspects of present invention can be any substance having an influence on one of the functions of Cathepsin C or on the Cathepsin C amount (protein or nucleic acid) in a cell, on Cathepsin C expression, posttranslational modification (e.g. N-glycosilation or processing (e.g. cleavage og the exclusion domain, e.g. at position 58 or 61)), oligomerization of the monomers, protein folding or activation.

To this end, the substance can modulate any of the functions of Cathepsin C (e.g. those as listed above or below). Cathepsin C protein activity can be modulated by the substance e.g. by direct interaction and interference of Cathepsin C polypeptide/protein or fragments thereof. The substance can also modulate Cathepsin C expression, e.g. on the level of transcription (initiation, elongation, processing, etc), transcript stability, translation. Moreover it can modulate the posttranslational modification, the processing from the inactive to the active form (cleavage of the prepro-form to the three polypeptides forming the active monomer) and/or the oligomerization from the monomeric to the tetrameric form, as well as protein folding etc. of Cathepsin C. The substance can exert the above effects directly or indirectly (indirectly meaning i.e. by interfering (positively or negatively) with natural signalling cascades having influence on Cathepsin C function/protein activity/expression etc.)

Functions of Cathepsin C comprise those as listed above, e.g. protease activity; the ability of removing dipeptides from the amino terminus of one or more protein substrates; the ability to interact specifically with one or more protein substrates (protein-protein interaction), such as those listed above; the ability to cleave and/or activate one or more protein substrates, such as those listed above; the ability to process protein substrates, such those listed above.

Functions of Cathepsin C comprise also generally the ability of Cathepsin C protein or nucleic acid or fragments thereof to interact with other molecules (comprising, but not limited to: proteins, nucleic acids, synthetic molecules) and preferably concern its capability of interacting and cleaving protein substrates.

Substrate of an enzyme is understood, within the terms of present application, to be any molecule that can be modified by the enzyme. Naturally occurring substrates in the scope of present invention are molecules that correspond to the form in which they occur in the natural physiological or pathological context (such as granule serine proteases, GZMA, GZMB), and which are also capable of being modified by the respective enzyme.

The modulation of pain can be either a decrease or an increase.

According to one aspect of present group of inter-related inventions, a fragment or derivative of Cathepsin C can be used. A fragment can be a fragment of a protein, polypeptide or polynucleic acid.

A fragment of a protein or polypeptide is a protein or polypeptide that carries one or more end-terminal (n- and/or c-terminal) and/or internal deletions of one, two or more amino acids, when compared to the full-length Cathepsin C; fragments comprise, e.g.

1. a Cathepsin C fragment carrying an n-terminal deletion of the dipeptide Xaa-Yaa, Zaa- in its Amino Acid chain, especially except when Xaa is Arg or Lys, or Yaa or Zaa is Pro;

2. a Cathepsin C fragment in which the Signal peptide (Amino Acids 1-24 of the Amino Acid chain) is deleted or Cathepsin C fragment consisting of amino acids 25-463
3. a Cathepsin C fragment comprising or consisting of positions 25-134 of the Amino Acid chain according to SEQ ID NO:2 (dipeptidyl-peptidase 1 exclusion domain chain)
4. a Cathepsin C fragment in which the propeptide (Amino Acids 135-230 is deleted)
5. a Cathepsin C fragment comprising or consisting of the dipeptidyl peptidase 1 heavy chain (Amino Acids 231-394);
6. a Cathepsin C fragment comprising or consisting of the dipeptidyl peptidase 1 light chain (Amino acids 395-463)
7. a Cathepsin C fragment comprising the dipeptidyl peptidase 1 light chain (Amino acids 395-463) and heavy chain (Amino Acids 231-394);
8. a Cathepsin C fragment comprising the dipeptidyl peptidase 1 light chain (Amino acids 395-463) and heavy chain (Amino Acids 231-394);

The positions of the above fragments refer to SEQ ID NO:2; preferred examples of the above fragments concern fragments of the protein according to SEQ ID NO:2.

A functional fragment of Cathepsin C protein is any fragment of this protein having at least one or more of the functional characteristics of the full-length protein, especially as listed above.

A fragment of a polynucleotide acid is a polynucleotide acid or an oligonucleotide carrying one or more end-terminal (5'- and/or 3'-) and/or internal deletions of one, two or more nucleotides, when compared to the full-length genomic or coding sequence. A functional fragment of Cathepsin C nucleic acid is any fragment having at least one or more of the functional characteristics of the full-length polynucleic acid (mRNA, genomic or coding sequence).

The term derivative of Cathepsin C comprises any type of modification of Cathepsin C in comparison to the naturally-occurring form, and especially in comparison to Cathepsin C according to SEQ ID NO:1 or SEQ ID NO 2, that is not a deletion. A functional derivative of Cathepsin C is any derivative of this protein having at least one and preferably two or more of the functional characteristics of the unmodified protein. Derivatives comprise, e.g. modifications of the amino acid or nucleotide sequence or any other kind of modification such as a chemical or biological modification leading e.g. to the stabilization of the polypeptide or polynucleotide (such as phosphoorothioate modifications of the nucleic acid backbone or of exchanges of the bonds between amino acids, etc), or enabling a specific targeting of the plypeptide or polynucleotide to certain cells or facilitating its entry into or its uptake by cells (such as cell-permanent phosphopeptides, ortho coupling to cell-permeant peptide vectors, e.g. based on the antennapedia/penetrating, TAT and signal-peptide based sequences; or coupling to parts of ligands for specific transporters or importers).

Present invention also comprises functional derivatives of fragments of Cathepsin C.

Another aspect of present invention concerns the use of a non-human transgenic animal heterologously expressing Cathepsin C or a functional fragment thereof for identifying or analyzing compounds that modulate pain.

The non human animal can be any non human animal. Preferred are rodents, such as rats or mice.

A transgenic animal is an animal that carries in its genome foreign DNA, which has deliberately been transferred thereto. The introduction of the foreign DNA into the animal genome can be performed according to standard procedures (see e.g. Transgenic Animal Technology A Laboratory Handbook. C. A. Pinkert, editor; Academic Press Inc., San Diego, Calif., 1994 (ISBN: 0125571658).

The term heterologous expression refers to an expression differing from the normal gene expression in the host organism (concerning steady state level, amount, timing or tissue distribution of the expressed gene or concerning the type of expressed gene (i.e. the gene is normally not expressed in the host at all)). The heterologous expression can be constitutive or inducible. Suitable inducible expression systems are well known in the art (e.g. the Tetracycline inducible system or the like). The organism can be a cell or a non-human animal.

According to another aspect, present invention concerns the use of a non-human transgenic animal heterologously expressing Cathepsin C or a functional fragment thereof as a model system for enhanced pain sensitivity.

Yet another aspect of present invention concerns the use of a non-human Cathepsin C knock-out animal for identifying or analyzing compounds that modulate pain.

A knock-out organism (such as an animal or a cell) refers to an organism in which the expression or function of a gene is partially or completely deleted and comprises genomic as well as functional knock outs, inducible as well as constitutive knock outs. The generation of knock out organisms is well known in the art, as well as cells or animals which can be used for generating knock out organisms. The generation of cathepsin C—knock out mice is described in Pham and Ley, 1999.

A further aspect of present invention concerns use of a non-human Cathepsin C knock-out animal as a model system for lowered pain sensitivity.

The use of a cell heterologously expressing Cathepsin C or a functional fragment thereof for identifying compounds that modulate pain, is another aspect of present invention.

The cell can be any prokaryotic or eucaryotic cell, such as cells capable of being transfected with a nucleic acid vector and of expressing a reporter gene. These comprise principally primary cells and cells from a cell culture, such as a eukaryotic cell culture comprising cells derived either from multicellular organisms and tissue (such as HeLA, CHO, COS, SF9 or 3T3 cells) or single cell organisms such as yeast (e.g. *S. pombe* or *S. cerevisiae*), or a procaryotic cell culture, preferably *Pichia* or *E. coli*. Cells and samples derived from tissue can be gained by well-known techniques, such as taking of blood, tissue punction or surgical techniques.

According to one embodiment, a modified cell, having a lower Cathepsin C activity as compared to its unmodified state, is used. This way, it can e.g. be tested, if the chemical compounds to be tested are able to enhance or restore the lowered or totally abolished Cathepsin C activity. Or it can be tested whether the substances are able to perform their function (e.g. pain modulation or even a function in the context of another diseased state or disease) in the context of lowered pain sensitivity.

The modification can be any type of modification (stable or transient, preferably stable), that leads to a decrease of Cathepsin C activity, Cathepsin C transcript steady state level (i.e. by activation of Cathepsin C transcription or transcript stabilisation) or Cathepsin C protein steady state level (i.e. by activation of Cathepsin C translation or its posttranslational processing; by modulation of Cathepsin C posttranslational modification or by activation of its stabilisation or by inhibition of its degradation). This can for example be achieved by using dominant negative mutants of Cathepsin C, antisense oligonucleotides, RNAi constructs of Cathepsin C, by generating functional or genomic Cathepsin C knock outs (which can e.g. be inducible) or other suitable techniques known within the state of the art. For an overview of the above techniques, see for example: Current protocols in Molecular biology (2000) J. G. Seidman, Chapter 23, Supplemtent 52, John Wiley and Sons, Inc.: Gene Targeting: a practical approach (1995), Editor: A. L. Joyner, IRL Press; Genetic Manipulation of Receptor Expression and Function, 2000; Antisense Therapeutics, 1996; Scherr et al, 2003.

According to one embodiment, a Cathepsin C knock-out cell is used. Suitable cell lines for the generation of knock-outs are well known in the state of the art, see e.g., Current protocols in Molecular Biology (2000) J. G. Seidman, Chapter 23, Supplement 52, John Wiley and Sons, Inc; or Gene Targeting a practical approach. (1995) Ed. A. L. Joyner, IRL Press. The generation of Cathepsin C (DPPI) knock-out cells is also published in Pham and Ley, 1999 (the generation of DPPI murine embryonic stem cell knock out clones, see page 8628, left column, upper half).

Another aspect of the invention concerns thus the use of a Cathepsin knock-out cell for identifying or analyzing compounds that modulate pain.

Furthermore, the use of a Cathepsin knock-out cell as a model system for lowered pain sensitivity, is another aspect of present group of inter-related inventions.

According to another embodiment of present invention, the cell can have a higher amount of Cathepsin C as compared to a reference cell (e.g. the same cell in its unmodified state). This cellular system can serve to mimic a state of enhanced pain sensitivity, as the amount of Cathepsin C expression is related to pain sensitivity.

Present invention relates thus also to the use of a cell heterologously expressing Cathepsin C or a functional fragment thereof as a model system for enhanced pain sensitivity.

The use of a cell heterologously expressing a reporter gene expressibly linked to the Cathepsin C promoter and/or enhancer or a functional fragment thereof for identifying or analyzing compounds that modulate pain.

The above aspect of present invention is based on a typical reporter gene assay commonly known in the art. To this end, the promoter of choice is inserted into an expression vector suitable for the type of host cell chosen, upstream of the reporter gene of choice in such a way as to allow for an expression of the reporter gene if the promoter is active. The construct is subsequently introduced into the host cell of choice. Suitable methods for transformation or transfection are well known in the art as well as conditions for cell cultivation and detection of reporter gene expression (see e.g. standard literature listed below). Suitable conditions are well known in the art as well as vectors, reporter genes and necessary reagents, which are also commercially available.

A vector is a circular or linear polynucleotide molecule, e.g. a DNA plasmid, bacteriophage or cosmid, by aid of which polynucleotide fragments (e.g. cut out from other vectors or amplified by PCR and inserted in the cloning vector) can specifically be amplified in suitable cells or organisms. Expression vectors enable the heterologous expression of a gene of interest (e.g. a reporter gene), in the host cell or organism. The type of cell or organism largely depends on the aim and the choice lies within the knowledge of the skilled artisan. Suitable organisms for the amplification of a nucleic acid are e.g. mostly single cell organisms with high proliferation rates, like e.g. bacteria or yeast. Suitable organisms can also be cells isolated and cultivated from multicellular tissues, like e.g. cell lines generated from diverse organisms (e.g. SF9 cells from *Spodoptera Frugiperda*, etc.). Suitable cloning vectors are known in the art and commercially available at diverse biotech suppliers like, e.g. Roche Diagnostics, New England Biolabs, Promega, Stratagene and many more. Suitable cell lines are e.g. commercially available at the American Type Culture Collection (ATCC).

For the heterologous expression of a protein or polypeptide, the cell can be any prokaryotic or eucaryotic cell capable of being transfected with a nucleic acid vector and of expressing the gene of interest, e.g. a reporter gene. These comprise principally primary cells and cells from a cell culture, preferably an eukaryotic cell culture comprising cells derived either from multicellular organisms and tissue (such as HEK293, RIN-5F, HeLA, CHO, COS, SF9 or 3T3 cells) or single cell organisms such as yeast (e.g. *S. pombe* or *S. cerevisiae*), or a procaryotic cell culture, preferably *Pichia* or *E. coli*. Cells and samples derived from tissue can be gained by well-known techniques, such as taking of blood, tissue punction or surgical techniques.

Within the context of present application, the term "transfection" refers to the introduction of a nucleic acid vector into a host cell (either prokaryotic or eucaryotic) and comprises thus the term "transformation".

The transfection can be a stable or transient transfection.

The Cathepsin C promoter is a part of the Cathepsin C gene able to drive expression of a gene product of interest if introduced into a suitable expression vector upstream of the coding sequence of the gene product. Preferably, the Cathepsin C promoter comprises or consists of the sequence according to nucleotides −1127 to +1 of the sequence as published by Rao et al., 1997, page 10263, FIG. 4. A functional fragment of the Cathepsin C promoter is any fragment of the Cathepsin C promoter that is able to drive expression of a gene product of interest if introduced into a suitable expression vector upstream of the coding sequence of the gene product. Preferable fragments comprise functional fragments of the Cathepsin C promoter as published by Rao et al., 1997, p. 10263, FIG. 4.

A reporter gene can be any gene that allows for an easy quantification of its gene product. A vast variety of reporter genes for eukaryotic or prokaryotic hosts as well as detection methods and necessary reagents are known in the art and commercially available. These comprise e.g. the genes of beta Lactamase (lacZ), Luciferase, Green or Blue fluorescent protein (GFP or BFP), DsRed, HIS3, URA3, TRP1 or LEU2 or beta Galactosidase. These genes encode proteins which can be easily detected by means of a visible (colour or luminescent) reaction (e.g. lacZ, Luciferase). These comprise gene-products which can be easily detected by means of a visible (colour or luminescent) reaction or gene-products conferring resistance towards antibiotics like Ampicillin or Kanamycin when expressed. Other reporter gene-products enable the expressing cells to grow under certain conditions like e.g. auxotrophic genes.

A functional fragment of a reporter gene is any fragment of a given reporter gene that allows for an easy quantification of its gene product.

The cell can be any prokaryotic or eucaryotic cell capable of being transfected with a nucleic acid vector and of expressing a reporter gene. These comprise principally primary cells and cells from a cell culture, preferably a eukaryotic cell culture comprising cells derived either from multicellular organisms and tissue (such as HeLA, CHO, COS, SF9 or 3T3 cells) or single cell organisms such as yeast (e.g. *S. pombe* or *S. cerevisiae*), or a procaryotic cell culture, preferably *Pichia* or *E. coli*. Cells and samples derived from tissue can be gained by well-known techniques, such as taking of blood, tissue punction or surgical techniques.

Within the context of the above aspect of present invention the control vector can be any suitable vector which comprises a reporter gene or functional fragment thereof, but wherein reporter gene expression is not driven by a (functional) Cathepsin C promoter. This can e.g. mean that the reporter gene or functional fragment thereof is not operationally coupled to a functional Cathepsin C promoter (i.e. either totally devoid of a Cathepsin C promotor, comprises a non functional Cathepsin C promoter or promoter fragment or wherein the coupling of promoter and reporter gene is not functional). Another possibility is that the reporter gene or functional fragment thereof is operationally coupled to another promoter than the Cathepsin C promoter (e.g. SV40 or another standard promoter). The functional vector and the control vector can also be transfected to the same cell, but in which case the reporter genes need to be different.

The identification of compounds according to the above uses can e.g. be performed according to assays as described below or as known in the art.

An assay is any type of analytical method or system to monitor a biological process. Suitably, molecular cascades and mechanisms representing parts of physiological metabolic pathways but also of pathological conditions are reproduced in cellular or biochemical (in vitro) systems. The pharmacological activity of a potential pharmaceutical compound can thus be determined according to its capability of interfering with or modulating these cascades or mechanisms.

For the use in drug screening, especially the high throughput screening for novel pharmaceutical compounds, the assay needs to be reproducible and is preferably also scalable and robust. In the scope of present invention, high throughput screen means, that a method according to present invention is performed in a very small scale, e.g. on 96, 386 or 1536 well plates in samples of very small volume in the range of few millilitres down to few nanoliters or even less. Thus, a very large amount of samples can be analysed in a short time. High throughput screening mostly comprises the screening of approximately 500.000 different compounds for a certain ability by means of one single assay. The assay is preferably suitable for high throughput screening of chemical substances for their ability of modulating the activity of the target molecule under investigation. The type of assay depends e.g. on the type of target molecule used (e.g. polypeptide or polynucleotide) and the "read out", i.e. the parameter, according to which the activity of the target molecule is determined (see below).

Different types of such assays are commonly known in the state of the art and commercially available from commercial suppliers.

Suitable assays for different purposes encompass radioisotopic or fluorescent assays, for example fluorescence polarization assays (such as those offered commercially by Panvera) or Packard BioScience (HTRF; ALPHAScreen™) for measuring the interaction of a labeled member with a non-labeled member (e.g. the interaction of labeled proteins with their unlabeled protein-ligands).

More examples include cell based assays, wherein a cell line stably (inducibly or not; chromosomal or episomal) or transiently expresses a recombinant protein of interest. These assays comprise e.g. reporter gene assays, wherein the regulation of a certain promotor or a signal transduction pathway of a member of a signal transduction cascade is measured according to the activity of a reporter enzyme, the expression of which is under the control of said certain promotor. For this type of assay, a recombinant cell line has to be constructed containing the reporter gene under the control of a defined promotor that is to be investigated itself or that is regulated by the signaling cascade under investigation. Suitable reporter enzymes are commonly known within the state of the art and comprise firefly luciferase, renilla luciferase (e.g. commercially available by Packard reagents), β-Galactosidase. Suitable cell lines depend on the aim of the assay but comprise mostly cell lines that are easy to transfect and easy to cultivate, such as, e.g. HeLA, COS, CHO, NIH-3T3, etc.

For determination of protease activity, typical protease assay formats are known: e.g. using a substrate carrying a reporter tag (e.g. a luminescent/fluorescent or other signal emitting protein/peptide or entity) at one position of the substrate and a quencher (an entitiy (e.g. another peptide inhibiting the signal emission of the reporter tag as long as the substrate is intact/uncleaved) at another position; the substrate is incubated with Cathepsin C under suitable conditions to allow for the cleavage of the substrate leading to the emission of a detectable signal (e.g. light-emission), because of the separation of quencher and reporter tag.

Other types of assays and other types of "read out" are well known in the state of the art.

Assays according to present invention concern:

A method of identifying or analyzing compounds modulating and/or preventing pain, comprising the steps
 a. Providing at least two samples;
 b. Contacting one sample containing Cathepsin C or a functional fragment or derivative thereof with a compound,
 c. determining the activity of Cathepsin C in the presence of compound,
 d. determining the activity of Cathepsin C in the absence of compound, and
 e. comparing the activity of Cathepsin C according to c) with that according to d).

A method for identifying or analyzing compounds that modulate and/or prevent pain comprising:
 a. Contacting a Cathepsin C protein or functional fragment or derivative thereof with a test compound; and
 b. Determining whether the test compound modulates the activity of the Cathepsin C protein or functional fragment or derivative thereof.

A method for identifying or analyzing compounds that modulate and/or prevent pain comprising:
 a. Contacting a cell, which has a detectable amount or activity of Cathepsin C or of a functional fragment or derivative thereof, with a test compound;
 b. Determining whether the test compound is able to modulate the amount or activity of Cathepsin C or the functional fragment or derivative thereof present in the cell.

A method for identifying or analyzing compounds that modulate and/or prevent pain comprising:
 a. Contacting a nucleic acid coding for a Cathepsin C protein or a functional fragment or derivative thereof with a test compound in a transcriptionally active system, and
 b. Determining the amount of mRNA coding for the Cathepsin C protein or the functional fragment or derivative thereof present in said system in presence of said compound, and
 c. Determining whether the compound is capable of modulating the amount of mRNA coding for the Cathepsin C protein or functional fragment or derivative present in said system.

A transcriptionally active system is any biochemical or cellular system which at least has the ability to perform a transcription reaction of a transcription unit. Such systems are well known in the art and comprise cells as well as in vitro transcription systems or kits (e.g. on basis of cell extracts) commercially available.

A method for identifying compounds or analyzing compounds that modulate and/or prevent pain comprising:

a. Providing a cell transfected with a nucleic acid vector comprising the promoter of a Cathepsin C gene or a functional fragment thereof operationally coupled to a reporter gene or a functional fragment thereof;
b. Providing a cell transfected with a control vector which comprises a reporter gene or a functional fragment thereof not being operationally coupled to a functional Cathepsin C promoter;
c. Determining the reporter gene activity of the cell according to a) and b) in the presence of a test compound;
d. Determining the reporter gene activity of the cell according to a) and b) in absence of the test compound.

A method for identifying or analyzing a compound that modulates pain comprising
a. Selecting a compound that modulates the activity of Cathepsin C as a test compound, and
b. Administering said test compound to a subject in sensation of pain to determine whether the pain is modulated.

A method of identifying or analyzing a compound that modulates and/or prevents pain in a subject comprising:
c. Assaying a biological activity of Cathepsin C or a functional fragment or derivative thereof in the presence of one or more test compounds to identify one or more modulating compounds that modulate the biological activity of Cathepsin C, and
d. Testing one or more of the modulating compounds for their ability to reduce pain, pain sensation or pain sensitivity in a subject.

Further aspects of present invention concern pharmacogenomic methods for classifying patient groups and assisting the physician to adapt/improve his treatment of individual patients, such as:

A method for analyzing the pain threshold in an individual comprising analyzing the amount of Cathepsin C in a taken sample of said individual in comparison to one or more reference samples as to whether the amount of Cathepsin C mRNA and/or protein present in said sample is different from that of one or more reference samples, wherein the presence of a higher amount indicates an increased pain sensitivity and the presence of a lower amount indicates a decreased pain sensitivity in said individual.

A method for adapting the dosage of a pharmaceutical for the prevention and/or treatment of pain in an individual, which method comprises examining a taken sample of an individual as to whether the amount of Cathepsin C mRNA and/or protein present in said sample is different from that of one or more reference samples, said dosage being adapted depending on whether the amount of protein and/or mRNA in the taken sample of the individual is different from that of the one or more reference samples, wherein a higher amount of Cathepsin C in the taken sample of the individual is indicative of a need for a higher dose and a lower amount of Cathepsin C in the sample of the individual is indicative of a need for a lower dose.

The term "taken sample" as used herein, refers to a biological sample taken/separated from the body of one or more individual beings (humans or non-human animals). Biological material and biological samples comprise, e.g. cells, preparations or parts of tissue or organs (e.g. brain, blood, liver, spleen, kidney, heart, blood vessels, etc.), preferably if derived from a vertebrate, and more preferably from a mammal including a human. Comprised are also cells from a cell culture, preferably a eukaryotic cell culture comprising cells derived either from multicellular organisms and tissue (such as HeLa, CHO, COS, SF9 or 3T3 cells) or single cell organisms such as yeast (e.g. *S. pombe* or *S. cerevisiae*), or a procaryotic cell culture, preferably *Pichia* or *E. coli*. Cells and samples derived from tissue can be gained by well-known techniques, such as taking of blood, tissue punction or surgical techniques. The preparation of recombinant molecules and the purification of naturally occurring molecules from cells or tissue, as well as the preparation of cell- or tissue extracts is well known to the person of skill in the art (see e.g. also the standard literature listed below).

The term "reference sample" refers to a biological sample taken from one or more individuals with a known given pain phenotype or to an in vitro biological sample (e.g. a sample stemming from in vitro cell or tissue culture (e.g. cultivated cells)) and corresponding in certain characteristics (e.g. its level of Cathepsin C activity, amount or expression) to a given pain phenotype (e.g. high pain sensitivity or low pain sensitivity).

Yet another aspect of present invention concerns the use of a means for the detection of Cathepsin C for determining enhanced pain sensitivity in an individual by analyzing a biological sample taken from the body of an individual to be examined.

The means for the detection of Cathepsin C can be any means able to specifically detect Cathepsin C polypeptide/protein or nucleic acid present in a biological sample.

A means to specifically detect Cathepsin C protein or polypeptide can be any means able to specifically detect either wildtype Cathepsin C protein/polypeptide and can also be a means to detect specifically Cathepsin C protein/polypeptide harbouring one or more mutations regarding the size or the amino acid sequence in comparison to a wild type polypeptide/protein. A preferred examply of such a means is an antibody able to specifically detect Cathepsin C protein, e.g. for use in immunohistological or immunohistochemical techniques (e.g. detection of Cathepsin C protein or certain mutations thereof in histological tissue sections or cathepsin C protein immobilized on suitable carriers like membranes, chips, ELISA plates etc.). CathepsinC antibodies are commercially available, such as Goat Anti-Human Cathepsin C, Catalog# AF1071, R&D Systems (Minneapolis, USA), Goat Anti-Mouse Cathepsin C, Catalog# BAF1034, R&D Systems (Minneapolis, USA).

The means to specifically detect Cathepsin C nucleic acid can e. g be a means to detect Cathepsin C mRNA/cDNA or genomic DNA, either wildtype or also harbouring one or more mutations regarding their length or their nucleic acid sequence in comparison to a wild type Cathepsin C nucleic acid. The means can e.g. be a means to specifically detect and/or quantify Cathepsin C mRNA and preferably comprises or is a specific Cathepsin C nucleic acid probe or a primer set capable of amplifying Cathepsin C DNA or, e.g. for use in PCR sequencing (for the detection of Mutations in the nucleotide sequence) or capable of amplifying Cathepsin C cDNA, e.g. for use in RT PCR (for the detection and/or quantification of Cathepsin C mRNA expression). Another means can e.g. be a nucleic acid probe able to specifically hybridise to Cathepsin C mRNA or cDNA under standard conditions, e.g. for use in Northern Blot or Chip hybridisation techniques.

The term wild type refers to the genotype or phenotype that is found in nature or in the standard laboratory stock for a given organism. According to one preferred embodiment, the wildtype sequences of Cathepsin C are the sequences according to SEQ ID NOs: 1, 2, 3.

The design and synthesis of suitable primers is well known in the art (see also above). According to a preferred embodiment of present invention, the means is a primer set for the amplification of Cathepsin C nucleic acid, such as human Cathepsin C nucleic acid, preferably a set of primers comprising at least one of the primers according to SEQ ID No. 4 and/or 5.

According to a further preferred embodiment of present invention, the means is a probe for the detection of Cathepsin C nucleic acid and preferably a probe having the sequence according to SEQ ID No. 6. The design and synthesis of suitable probes is well known in the art (see also standard literature below).

According to yet another preferred embodiment of present invention, the means is an antibody for the specific detection of Cathepsin C protein or polypeptide. The preparation of suitable antibodies or functional fragments thereof is well known in the art as well, e.g. by immunizing a mammal, for example a rabbit, with Cathepsin C protein or a fragment thereof, where appropriate in the presence of, for example, Freund's adjuvant and/or aluminium hydroxide gels (see, for example, Diamond, B. A. et al. (1981) The New England Journal of Medicine: 1344-1349). The polyclonal antibodies which are formed in the animal as a result of an immunological reaction can subsequently be isolated from the blood using well-known methods and, for example, purified by means of column chromatography. Monoclonal antibodies can, for example, be prepared in accordance with the known method of Winter & Milstein (Winter, G. & Milstein, C. (1991) Nature, 349, 293-299). Suitable procedures to produce monoclonal antibodies are well known in the art as well (see e.g. literature for standard methods listed below). In the context of present invention, the term antibody or antibody fragment comprises also antibodies or antigen-binding parts thereof, which have been prepared recombinantly and, where appropriate, modified, such as chimaeric antibodies, humanized antibodies, multifunctional antibodies, bispecific or oligospecific antibodies, single-stranded antibodies and F(ab) or F(ab)$_2$ fragments (see, for example, EP-B1-0 368 684, U.S. Pat. Nos. 4,816,567, 4,816,397, WO 88/01649, WO 93/06213 or WO 98/24884).

Another aspect of present invention concerns a diagnostic kit for determining the pain sensitivity in an individual, which test kit comprises at least one means for the detection of Cathepsin C in a biological sample.

In the context of the present invention, a test kit is understood to be any combination of the components identified in this application, which are combined, coexisting spatially, to a functional unit, and which can contain further components.

In the context of present invention, a test kit comprises at least a means for detection of Cathepsin C (e.g. amount/or mutation) in a biological sample, suitably together with suitable buffers and/or reagents for performing a detection reaction (e.g. immunological detection of Cathepsin C by means of an antibody, an enzymatic reaction for assaying Cathepsin C activity or the like), and/or sample preparation, and optionally a handling manual for performing the respective detection technique.

Other aspects of present invention concern methods of treatment, such as:

A method for treating pain in a subject that is experiencing pain comprising administering to said subject a therapeutically effective amount of a composition lowering the amount or activity of Cathepsin C in said subject. This can be the amount or activity of Cathepsin C altogether or in a certain tissue, e.g. in neural tissue, in lymphatic tissue or cells of the immune system such as mast cells, macrophages, neutrophils, T-cells (such as CD8+ T-cells), etc. wherein a therapeutically effective amount comprises an amount sufficient to ameliorate the pain sensation or sensitivity in the individual.

A method for lowering the pain sensitivity in a subject comprising administering to said subject a therapeutically effective amount of a composition lowering the amount (e.g. expression, half life) or activity of Cathepsin C in said subject (e.g. in lymphatic or neural tissue or cells of the immune system), concerns yet another aspect of present invention.

Moreover, present invention concerns a method for modulating the pain sensitivity in an offspring from a non-human female subject comprising transferring (e.g. electroporating) a nucleic acid conferring a modulated Cathepsin C expression into Zygotes, transferring the Zygotes into a non-human foster mother and electing offspring according to its Cathepsin C expression characteristics (lowered or abolished cathepsin C expression in comparison with wild type subjects, such as mice).

Another aspect of present invention concerns a compound that is able to lower Cathepsin C activity and/or expression for the treatment of pain.

Inhibitors of Cathepsin C are known in the art, such as peptide nitrile inhibitors (see e.g. Methot et al., 2007, which is incorporated herein by reference, see especially page 20839, FIG. 1 for structures of different Cathepsin C-inhibitors, such as Gly-Phe-DMK, Gly4-(I) Phe-DMK and compound 1* and compound 2* of said figure).

For the production of the medicament the modulators of Cathepsin C of the present invention can be formulated with suitable additives or auxiliary substances, such as physiological buffer solution, e.g. sodium chloride solution, demineralized water, stabilizers, such as protease or nuclease inhibitors, preferably aprotinin, ε-aminocaproic acid or pepstatin A or sequestering agents such as EDTA, gel formulations, such as white vaseline, low-viscosity paraffin and/or yellow wax, etc. depending on the kind of administration.

Suitable further additives are, for example, detergents, such as, for example, Triton X-100 or sodium deoxycholate, but also polyols, such as, for example, polyethylene glycol or glycerol, sugars, such as, for example, sucrose or glucose, zwitterionic compounds, such as, for example, amino acids such as glycine or in particular taurine or betaine and/or a protein, such as, for example, bovine or human serum albumin. Detergents, polyols and/or zwitterionic compounds are preferred.

The physiological buffer solution preferably has a pH of approx. 6.0-8.0, especially a pH of approx. 6.8-7.8, in particular a pH of approx. 7.4, and/or an osmolarity of approx. 200-400 milliosmol/liter, preferably of approx. 290-310 milliosmol/liter. The pH of the medicament is in general adjusted using a suitable organic or inorganic buffer, such as, for example, preferably using a phosphate buffer, tris buffer (tris (hydroxymethyl)aminomethane), HEPES buffer ([4-(2-hydroxyethyl)piperazino]ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions.

The medicament can be administered in a conventional manner, e.g. by means of oral dosage forms, such as, for example, tablets or capsules, by means of the mucous membranes, for example the nose or the oral cavity, in the form of dispositories implanted under the skin, by means of injections, infusions or gels which contain the medicaments according to the invention. It is further possible to administer the medicament topically and locally in order to treat the particular joint disease as described above, if appropriate, in the form of liposome complexes. Furthermore, the treatment can be carried out by means of a transdermal therapeutic system (US), which makes possible a temporally controlled release of the medicaments. TTS are known for example, from EP 0 944 398 A1, EP 0 916 336 A1, EP 0 889 723 A1 or EP 0 852 493 A1.

Injection solutions are in general used if only relatively small amounts of a solution or suspension, for example about 1 to about 20 ml, are to be administered to the body. Infusion solutions are in general used if a larger amount of a solution or suspension, for example one or more litres, are to be administered. Since, in contrast to the infusion solution, only a few millilitres are administered in the case of injection solutions, small differences from the pH and from the osmotic pressure of the blood or the tissue fluid in the injection do not make themselves noticeable or only make themselves noticeable to an insignificant extent with respect to pain sensation. Dilution of the formulation according to the invention before use is therefore in general not necessary. In the case of the administration of relatively large amounts, however, the formulation according to the invention should be diluted briefly before administration to such an extent that an at least approximately isotonic solution is obtained. An example of an isotonic solution is a 0.9% strength sodium chloride solution. In the case of infusion, the dilution can be carried out, for example, using sterile water while the administration can be carried out, for example, via a so-called bypass.

According to one preferred embodiment of the different aspects of present invention, Cathepsin C, the derivative or fragment thereof can be used as an isolated molecule.

In the context of this invention, the term "isolated molecule", especially with respect to Cathepsin C, refers to Cathepsin C polynucleotides or polypeptides purified from natural sources as well as purified recombinant molecules (wherein the term purified comprises a partial purification as well as a complete purification).

The preparation of recombinant polypeptide or polynucleotide molecules and the purification of naturally occurring molecules from cells or tissue, as well as the preparation of cell- or tissue extracts is well known to the person of skill in the art (see e.g. also the standard literature listed below).

These comprise e.g. amplifying polynucleotides of desired length via the polymerase chain reaction (PCR) on the basis of the published genomic or coding polynucleotide sequences and the subsequent cloning of the produced polynucleotides in host cells (see e.g. standard literature listed below).

In the context of present invention, the term "polypeptide" refers to a molecule comprising amino acids bound to each other by peptide bonds containing at least 50 amino acids coupled to each other in a linear mode to form a polypeptide chain. Shorter molecules of this kind are referred to as peptides. The term "protein" refers to molecules comprising at least one polypeptide chain but can refer also to molecules comprising more than one polypeptide chains associated or bound to each other. Thus, the term "protein" comprises the term "polypeptide".

In the following, the invention is explained in more detail by means of examples without meaning to be limited by them.

EXAMPLES

Materials and Methods:
Mouse Strains Used:
Five different inbred mouse strains were used: AKR/J (AKR), CBA/J (CBA), C3H/HeJ (C3H), C57BL/6J (B6) and C58/J (C58). Mice were obtained from The Jackson Laboratory (Bar Harbor, Me., USA). For these mice strains it has been shown that they differ significantly concerning several in vivo measures of pain (Mogil et al 1999)

Total RNA Isolation:
Total RNA from DRGs (dorsal root ganglia) was isolated with the PicoPure™ RNA Isolation Kit (Arcturus) following the manufacturer's instructions. RNA quality was assessed using the 2100 Bioanalyzer and RNA 6000 Nano LabChip™ kit (Agilent).

Affymetrix GeneChip™ Microarrays:
First-strand cDNA synthesis was performed using 500 ng total RNA with a 100 pM T7-(dT)24 oligomer (GGCCAGT-GAATTGTAATACGACTCACTATAGGGAGGCGG-dT$_{24}$ SEQ ID NO:4) according to Baugh, L. R, Hill, A. A., Brown, E. L. and Hunter, C. P. (2001) Nucleic Acids Res. 29, e29 and SuperScript II Reverse Transcriptase following the manufacturer's instructions. Double-stranded cDNA was synthesized and then extracted using phenol-chloroform followed by an ethanol precipitation step. An in vitro transcription reaction was performed with the doublestranded cDNA sample using the BioArray High Yield RNA Transcription Labeling kit (Enzo) according to the manufacturer's instructions. Transcription reactions were incubated at 37° C. for 16 h. cRNA was purified using the RNeasy™ Mini kit (Qiagen) protocol for RNA cleanup and quantified by a spectrophotometer. The biotin-labeled cRNA was fragmented using a RNA fragmentation buffer (200 mM Tris-acetate, 500 mM KOAc, 150 mM MgOAc, pH 8.1). Hybridization and staining of Mouse Genome 430 2.0 GeneChips™ (Affymetrix) was performed according to the manufacturer's instructions. The microarrays were scanned using a GeneChip™ 3000 Scanner, and the scanned data were imported and analyzed using Resolver v5.1 expression data analysis software (Rosetta Biosoftware).

L5 Spinal Nerve Transection and Sham Surgical Procedures:
In anesthetized mice, the left L5 spinal nerve was exposed and the transverse process was then partially removed. After separation from the L4 spinal nerve, the L5 spinal nerve was transected. Sham surgery was identical to the L5 spinal nerve transection surgery, however, the L5 spinal nerve was not transected (see DeLeo et al. 2000).

Determination of Paw Withdrawal Threshold:
Paw withdrawal thresholds (PWTs) were assessed using a dynamic plantar aesthesiometer (see Szabo et al. 2005). After acclimation in a compartment with metal mesh floor, the stimulator was positioned under the animal's hindpaw, a straight metal filament driven by an electrodynamic actuator touched the plantar surface and exerted an increasing upward force until the animal removed the paw (paw withdrawal threshold, PWT). PWTs were assessed for hindpaws of the ipsilateral, operated side and of the contralateral side. Each animal was used at one occasion only. In all animal experiments the ethics guidelines for investigations in conscious animals were obeyed, and the procedures were approved by the local Ethics Committee Correlational Analysis:
For correlational analysis, the "pain phenotype" was defined for each nerve-transsected animal (Chung animal) as C1-S1, where C1=ln(ipsilateral PWT/contralateral PWT) and S1=mean$_{all\ sham\ animals\ within\ same\ strain}$ ln(ipsilateral PWT/contralateral PWT).

Two measures of differential transcriptional regulation were defined for each Chung animal and each measured gene based on its intensity expression data. The "raw intensity measure" was taken as the intensity measure computed by the Resolver expression data analysis software (v5.1) for the respective gene and animal. The "log ratio measure" was computed for a specific gene and Chung animal as ln(C2/S2), where C2=Chung expression intensity and S2=mean$_{all\ sham\ animals\ within\ same\ strain}$ Sham expression intensity.

Before correlations were computed, the set of genes was filtered to exclude genes that were expressed below noise level and without significant Chung vs. sham regulation. Eligible genes must be regulated in at least 60% of Chung animals with an absolute fold-change=>1.5 or in at least 20% of Chung animals with an absolute fold-change=>2.0. Also, corresponding gene expression had to be detectable ("present") in at least five animals as defined by a respective intensity p-value<0.001.

Pearson correlation coefficients for each gene between the pain phenotypic scores and one of the defined measures of transcriptional regulation were computed using the R software package (http://www.r-project.org/). Based on these, p-values of statistical significance and corresponding false-discovery rates (FDRs) were generated following the method of Storey et al. (2002). Genes with FDR<0.05 under "log ratio measure" or "intensity measure" were considered significantly correlated.

LEGEND TO THE FIGURES

FIG. 1: CathepsinC—Correlation Plot

FIG. 1 shows for every individual mouse its neuropathic pain phenotype (mechanical hypersensitivity, X-axis) and the corresponding gene regulation of Cathepsin C (log ratio (Chung vs. Sham control), Y-axis) in the L5 DRG. Mouse data are colour-coded depending on the used strain. A Pearson correlation analysis has been performed and revealed a significant positive correlation of the two parameters pain phenotype and Cathepsin C gene regulation. This means for individual mice that the higher the L5 DRG expression of Cathepsin C in Chung-operated neuropathic mice was, the more pronounced the mechanical hyperalgesia as exhibited in the behavioral test. This significant correlation indicates a causal relationship of Cathepsin C gene expression for the induction of the neuropathic pain phenotype.

FIG. 2: Cathepsin C—Intensity data

Absolute values of Cathepsin C expression in L5 ganglia of the individual mice of the strains AKR, CBA and C57 after chung or sham surgery.

FIG. 3: Fragment of mouse Cathepsin C mRNA, detected by the Affymetrix probe set 1416382_at (Mouse Genome 430 2.0 microarray) (SEQ ID NO. 7)

FIG. 4: Cathepsin C cDNA sequence according to NM_001814 (SEQ ID NO. 1)

FIG. 5: Cathepsin C protein sequence according to Swiss-Prot HUMAN_CATC P53634 (SEQ ID NO. 2)

FIG. 6: Primer set for Detection of human Cathepsin C cDNA according to SEQ ID NO. 1 (SEQ ID NOs 4 and 5).

FIG. 7: Probe for detecting mouse Cathepsin C cDNA (SEQ ID NO. 6).

REFERENCES

DeLeo J A et al (2000) Transgenic expression of TNF by astrocytes increases mechanical allodynia in a mouse neuropathy model. Neuroreport 11:599-602.

Storey J D. (2002) A direct approach to false discovery rates. Journal of the Royal Statistical Society, Series B, 64: 479-498.

Szabo A et al. (2005) Role of transient receptor potential vanilloid 1 receptors in adjuvant-induced chronic arthritis: in vivo study using gene-deficient mice. J. Pharmacol. Exp. Ther. 314:111-119.

Julius and Basbaum "Molecular mechanisms of nociception", Nature, volume 413, 13. September 2001, pp. 203-209;

Scholz and Woolf "Can we conquer pain", Nature neuroscience supplement, volume 5, November 2002, pp. 1062-1067;

Wood, J. D. "Pathobiology of Visceral Pain: Molecular Mechanisms and Therapeutic Implications II. genetic approaches to pain therapy", American Journal pf Physiological Gastrointestinal Liver Physiology, 2000, volume 278, G507-G512;

Woolf and Mannion "Neuropathic pain: aetiology, symptoms mechanisms, and management", The LANCET, volume 353, Jun. 5, 1999, pp. 1959-1964;

Woolf J. and Salter M. W. "Neuronal Plasticity: Increasing the Gain in Pain", Science, volume 288, Jun. 9, 2000, pp. 1765-1768;

Cigic, B.; Dahl, S. W.; Pain, R. H. "The residual pro-part of cathepsin C fulfills the criteria required for an intramolecular chaperone in folding and stabilizing the human proenzyme". Biochemistry 39: 12382-12390, 2000

Paris, A.; Strukelj, B.; Pungercar, J.; Renko, M.; Dolenc, I.; Turk, V.: "Molecular cloning and sequence analysis of human preprocathepsin C". FEBS Lett. 369: 326-330, 1995

Pham, C. T. N.; Armstrong, R. J.; Zimonjic, D. B.; Popescu, N. C.; Payan, D. G.; Ley, T. J. "Molecular cloning, chromosomal localization, and expression of murine dipeptidyl peptidase I" J. Biol. Chem. 272: 10695-10703, 1997.

Pham, C. T. N.; Ley, T. J.: "Dipeptidyl peptidase I is required for the processing and activation of granzymes A and B in vivo". Proc. Nat. Acad. Sci. 96: 8627-8632, 1999.

Rao, N. V.; Rao, G. V.; Hoidal, J. R.: "Human dipeptidyl-peptidase I". J. Biol. Chem. 272: 10260-10265, 1997.

Toomes, C.; James, J.; Wood, A. J.; Wu, C. L.; McCormick, D.; Lench, N.; Hewitt, C.; Moynihan, L.; Roberts, E.; Woods, C. G.; Markham, A.; Wong, M.; and 10 others: "Loss-of-function mutations in the cathepsin C gene result in periodontal disease and palmoplantar keratosis". Nature Genet. 23: 421-424, 1999.

Wolters, P. J.; Raymond, W. W.; Blount, J. L.; Caughey, G. H.:"Regulated expression, processing, and secretion of dog mast cell dipeptidyl peptidase I." J. Biol. Chem. 273: 15514-15520, 1998

Heusel, J. W., Wesselschmidt, R., Shresta, S., Russel, J & Ley, T. J. "Cytotoxic lymphocytes require granzyme B for the rapid induction of DNA fragmentation and apoptosis in allogeneic target cells", 1994, Cell 76, 977-987.

Manour, S., Thomas, K. R., and Capecchi, M. R., 1989, "disruption of the proto-oncogene Int-2 in mouse embryo-derived stem cells: a general strategy for targeting mutations so non-selectable genes", Nature 336, 348-352.

Soriano, P I, Montgomery, C., Geske, R., and Bradley, A., 1991, "Targeted disruption of the c-src proto-oncogene leads to osteopetrosis in mice", Cell 65, 693-702.

Turk, B., Turk, D., and Turk, V., Lysosomal cysteine proteases: more than scavengers. Biochim Biophys Acta. 2000 Mar. 7; 1477(1-2):98-111.

McGuire, M., J., Lipsky, P. E., and Thiele, D. L. (1993) J. Biol. Chem., 268, 2458-2467, Generation of active myeloid and lymphoid granule serine proteases requires processing by the granule thiol protease dipeptidyl peptidase I.

Henningsson, F., wolters, P., Chapman, H. A., Caughey, G. H., and Peijler, G., (2003), Biol., Chem. 384, 1527-1531, Mast cell cathepsins C and S control levels of carboxypeptidase A and the chymase, mouse mast cell protease 5.

Adkison, A. M., Raptis, S. Z., Kelley, D. G., and Pham, C. T. N., (2002), J. Clin. Invest. 109, 363-371, Dipeptidyl peptidase I activates neutrophil-derived serine proteases and regulates the development of acute experimental arthritis.

Wolters, P. J., Pham, C. T. N., Muilenburg, D. J., ley, T. J., and Caughey, G. H., (20019 j: Biol: Chem., 276, 18551-18556, Dipeptidyl peptidase I is essential for activation of mast cell chymases, but not tryptases, in mice.

Pham, C. T. N., Ivanovich, M. L., Raptis, S. Z., Zehnbauer, B., and Ley, T. J., (2004) J. Immunol., 173, 7277-7281, Papillon-Lefèvre syndrome: correlating the molecular, cellular, and clinical consequences of cathepsin C/dipeptidyl peptidase I deficiency in humans.

De Haar, S. F., Jansen, D. C., Schoenmaker, T., De Vree, H., Everts, V., and Beertsen, W. (2004) Hum. Mutat. 23, 524-524, Loss-of-function mutations in cathepsin C in two families with Papillon-Lefèvre syndrome are associated with deficiency of serine proteinases in PMNs.

Sheth, P. D., Pedersen, N M., Walls, A. F., and McEuen, A. R. (2003) Biochem., Pharmacol., 66, 2251-2262, Inhibition of dipeptidyl peptidase I in the human mast cell line HMC-1: blocked activation of tryptase, but not of the predominant chymotryptic activity.

Literature for Standard Laboratory Methods

If not indicated otherwise, standard laboratory methods were or can be performed according to the following standard literature:

Sambrook et al. (1989) Molecular Cloning: A Laboratory Manual. Second edition. Cold Spring Harbor Laboratory Press, Cold Spring Harbor, N.Y. 545 pp;

Current Protocols in Molecular Biology; regularly updated, e.g. Volume 2000; Wiley & Sons, Inc; Editors: Fred M. Ausubel, Roger Brent, Robert Eg. Kingston, David D. Moore, J. G. Seidman, John A. Smith, Kevin Struhl.

Current Protocols in Human Genetics; regularly uptdated; Wiley & Sons, Inc; Editors: Nicholas C. Dracopoli, Honathan L. Haines, Bruce R. Korf, Cynthia C. Morton, Christine E. Seidman, J. G. Seigman, Douglas R. Smith.

Current Protocols in Protein Science; regularly updated; Wiley & Sons, Inc; Editors: John E. Coligan, Ben M. Dunn, Hidde L. Ploegh, David W. Speicher, Paul T. Wingfield.

Molecular Biology of the Cell; third edition; Alberts, B., Bray, D., Lewis, J., Raff, M., Roberts, K., Watson, J. D.; Garland Publishing, Inc. New York & London, 1994;

Short Protocols in Molecular Biology, 5th edition, by Frederick M. Ansubel (Editor), Roger Brent (Editor), Robert E. Kingston (Editor), David D. Moore (Editor), J. G. Seidman (Editor), John A. Smith (Editor), Kevin Struhl (Editor), October 2002, John Wiley & Sons, Inc., New York;

Transgenic Animal Technology A Laboratory Handboook. C. A. Pinkert, editor; Academic Press Inc., San Diego, Calif., 1994 (ISBN: 0125571658)

Gene targeting: A Practical Approach, $2^{nd}$ Ed., Joyner A L, ed. 2000. IRL Press at Oxford University Press, New York;

Manipulating the Mouse Embryo: A Laboratory Manual. Nagy, A, Gertsenstein, M., Vintersten, K., Behringer, R., 2003, Cold Spring Harbor Press, New York;

Remington's Pharmaceutical Sciences, $17^{th}$ Edition, 1985 (for physiologically tolerable salts (anorganic or organic), see esp. p. 1418)

Standard Literature for Laboratory Methods:

If not indicated otherwise, laboratory methods were or can be performed according to standard methods listed in the below standard literature:

Sambrook et al. (1989) Molecular Cloning: A Laboratory Manual. Second edition. Cold Spring Harbor Laboratory Press, Cold Spring Harbor, N.Y. 545 pp or Current Protocols in Molecular Biology;

Current Protocols in Molecular Biology; regularly updated, e.g. Volume 2000; John Wiley & Sons, Inc; Editors: Fred M. Ausubel, Roger Brent, Robert Eg. Kingston, David D. Moore, J. G. Seidman, John A. Smith, Kevin Struhl.

Current Protocols in Human Genetics; regularly uptdated, e.g. Volume 2003; John Wiley & Sons, Inc; Editors: Nicholas C. Dracopoli, Honathan L. Haines, Bruce R. Korf, Cynthia C. Morton, Christine E. Seidman, J. G. Seigman, Douglas R. Smith.

Current Protocols in Protein Science; regularly updated, e.g. Volume 2003; John Wiley & Sons, Inc; Editors: John E. Coligan, Ben M. Dunn, Hidde L. Ploegh, David W. Speicher, Paul T. Wingfield.

Molecular Biology of the Cell; third edition; Alberts, B., Bray, D., Lewis, J., Raff, M., Roberts, K., Watson, J. D.; Garland Publishing, Inc. New York & London, 1994;

Gene Targeting: a practical approach (1995), Editor: A. L. Joyner, IRL Press

Remington's Pharmaceutical Sciences, Edition 17, 1985.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08349567B2). An electronic copy of the "Sequence Listing" will also be available from the USPTO upon request and payment of the fee set forth in 37 CFR 1.19(b)(3).

The invention claimed is:

1. A method for identifying a compound that reduces pain comprising:

a. providing a test cell transfected with a nucleic acid vector comprising the promoter of a Cathepsin C gene operably linked to a reporter gene;

b. determining the reporter gene activity of the test cells in the presence of a test compound;

c. determining the reporter gene activity of the test cells in absence of the test compound; and d. comparing the reporter gene activity of the test cells in the presence of the test compound to the reporter gene activity of the test cells in the absence of the test compound, wherein a decrease in activity of the reporter gene in the test cell in the presence of the test compound as compared to the activity of the reporter gene in the test cell in the absence of the test compound indicates that the test compound will reduce pain.

2. The method of claim 1, wherein the reporter gene is selected from the group consisting of beta lactamase (LacZ), luciferase, green fluorescent protein (GFP), blue fluorescent protein (BFP), DsRed, HIS3, URA3, TRP1, LEU2, and beta galactosidase.

3. A method for identifying a compound that reduces pain comprising:
   a. contacting a nucleic acid coding for a Cathepsin C protein with a test compound in a transcriptionally active system;
   b. determining the amount of mRNA coding for the Cathepsin C protein that is present in the system in the presence of the test compound;
   c. determining the amount of mRNA coding for the Cathepsin C protein that is present in the system in the absence of the test compound; and
   d. comparing the amount of mRNA that is present in the system in the presence of the test compound to the amount of mRNA that is present in the system in the absence of the test compound, wherein decreased expression of mRNA in the presence of the test compound as compared to the expression level of mRNA in the absence of the test compound indicates that the test compound will reduce pain.

4. The method of claim 3, wherein a cell expressing recombinant Cathepsin C is used.

5. The method of claim 4, wherein Cathepsin C is encoded by a polynucleotide selected from the group consisting of:
   a. a polynucleotide comprising the nucleic acid sequence of SEQ ID NO: 1, and
   b. a polynucleotide coding for the Cathepsin C protein of SEQ ID NO: 2.

6. A method for identifying a compound that reduces pain comprising:
   a. providing a test cell transfected with a nucleic acid vector comprising the promoter of a Cathepsin C gene operably linked to a reporter gene;
   b. providing a control cell transfected with a control vector comprising a reporter gene that is not operably linked to the promoter of a Cathepsin C gene;
   c. determining the reporter gene activity of each of the cells in steps a) and b) in the presence of a test compound; and
   d. comparing the reporter gene activity of the test cell in the presence of the test compound to the reporter gene activity of the control cell in the presence of the test compound, wherein decreased activity of the reporter gene in the test cell in the presence of the test compound as compared to the activity of the reporter gene in the control cell in the presence of the test compound indicates that the test compound will reduce pain.

7. The method of claim 6, wherein the reporter gene is selected from the group consisting of beta lactamase (LacZ), luciferase, green fluorescent protein (GFP), blue fluorescent protein (BFP), DsRed, HIS3, URA3, TRP1, LEU2, and beta galactosidase.

* * * * *

UNITED STATES PATENT AND TRADEMARK OFFICE
CERTIFICATE OF CORRECTION

PATENT NO. : 8,349,567 B2
APPLICATION NO. : 12/934178
DATED : January 8, 2013
INVENTOR(S) : Mathias Gebauer et al.

It is certified that error appears in the above-identified patent and that said Letters Patent is hereby corrected as shown below:

On the Title page, in item (56), in column 2, under "Other Publications", line 16, delete "funtion" and insert -- function --, therefor.

On the Title page, in item (56), in column 2, under "Other Publications", line 18-19, delete "Mutationin Brief" and insert -- Mutation in Brief --, therefor.

On the Title page, in item (56), in column 2, under "Other Publications", line 44, delete "Jul. 1998," and insert -- Jul. 1999, --, therefor.

Title page 2, column 1, under "Other Publications", line 10, delete "Osetopetrosis" and insert -- Osteopetrosis --, therefor.

In the Specifications:

In column 2, line 24, delete "C)" and insert - - C). - -, therefor.

In column 2, line 54, delete "orq.)," and insert - - org.), - -, therefor.

In column 2, line 64, delete "adress:" and insert - - address: - -, therefor.

In column 2, line 64, delete "qov)." and insert - - gov). - -, therefor.

In column 3, line 3, delete "5"flanking" and insert - - 5' flanking - -, therefor.

In column 4, line 10, delete "N-glycosilation" and insert - - N-glucosylation - -, therefor.

In column 4, line 11, delete "og" and insert - - of - -, therefor.

Signed and Sealed this
Sixth Day of August, 2013

Teresa Stanek Rea
*Acting Director of the United States Patent and Trademark Office*

CERTIFICATE OF CORRECTION (continued)
U.S. Pat. No. 8,349,567 B2

In column 5, line 46, delete "phosphoorothioate" and insert -- phosphorothioate --, therefor.

In column 5, line 48, delete "plypeptide" and insert -- polypeptide --, therefor.

In column 5, line 51, delete "cell-permeant" and insert -- cell-permanent --, therefor.

In column 6, line 41, delete "procaryotic" and insert -- prokaryotic --, therefor.

In column 6, line 44, delete "punction" and insert -- function --, therefor.

In column 7, line 2, delete "Supplemtent" and insert -- Supplement --, therefor.

In column 7, line 3, delete "Inc.:" and insert -- Inc.; --, therefor.

In column 8, line 12, delete "procaryotic" and insert -- prokaryotic --, therefor.

In column 8, line 14-15, delete "punction" and insert -- function --, therefor.

In column 8, line 61, delete "procaryotic" and insert -- prokaryotic --, therefor.

In column 8, line 64, delete "punction" and insert -- function --, therefor.

In column 10, line 9, delete "entitiy" and insert -- entity --, therefor.

In column 11, line 67, delete "procaryotic" and insert -- prokaryotic --, therefor.

In column 12, line 2, delete "punction" and insert -- function --, therefor.

In column 14, line 67, delete "(US)," and insert -- (TTS), --, therefor.

In column 15, line 67, delete "1999)" and insert -- 1999). --, therefor.

In column 16, line 52, delete "Committee" and insert -- Committee. --, therefor.

In column 16, line 55, delete "nerve-transsected" and insert -- nerve-transected --, therefor.

In column 18, line 6, delete "pf" and insert -- of --, therefor.

In column 19, line 36, delete "uptdated;" and insert -- updated; --, therefor.

In column 20, line 6, delete "Handboook." and insert -- Handbook. --, therefor.

In column 20, line 31, delete "uptdated," and insert -- updated, --, therefor.